United States Patent
Xu et al.

(10) Patent No.: US 10,729,642 B2
(45) Date of Patent: Aug. 4, 2020

(54) NAIL CARE SYSTEM (71) Applicant: L'ORÉAL, Paris (FR)

(72) Inventors: Ruisong Xu, Solon, OH (US); Aline Aude Guimont, Westfield, NJ (US); Allen Sha, Los Angeles, CA (US); Ramakrishnan Hariharan, Springfield, NJ (US); Chaitrali Makarand Gothe, Newark, CA (US); Christopher John Tarling, Brooklyn, NY (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/934,314

(22) Filed: Mar. 23, 2018

(65) Prior Publication Data
US 2018/0207084 A1  Jul. 26, 2018

Related U.S. Application Data (63) Continuation of application No. 14/931,400, filed on Nov. 3, 2015, now Pat. No. 9,962,328.

(51) Int. Cl.
| | |
|---|---|
| *A45D 34/04* | (2006.01) |
| *A61K 8/895* | (2006.01) |
| *A61Q 3/02* | (2006.01) |
| *A61K 8/88* | (2006.01) |
| *A61K 8/891* | (2006.01) |
| *A61K 8/34* | (2006.01) |
| *A61K 8/37* | (2006.01) |
| *A61K 8/73* | (2006.01) |
| *A61K 8/29* | (2006.01) |
| *A61K 8/23* | (2006.01) |
| *A61K 8/97* | (2017.01) |
| *A61K 8/81* | (2006.01) |
| *A61K 8/46* | (2006.01) |
| *A61K 8/365* | (2006.01) |
| *A61K 8/86* | (2006.01) |
| *A61K 8/87* | (2006.01) |

(52) U.S. Cl.
CPC ............ *A61K 8/895* (2013.01); *A45D 34/045* (2013.01); *A61K 8/23* (2013.01); *A61K 8/29* (2013.01); *A61K 8/34* (2013.01); *A61K 8/365* (2013.01); *A61K 8/37* (2013.01); *A61K 8/466* (2013.01); *A61K 8/731* (2013.01); *A61K 8/8111* (2013.01); *A61K 8/8117* (2013.01); *A61K 8/86* (2013.01); *A61K 8/87* (2013.01); *A61K 8/88* (2013.01); *A61K 8/891* (2013.01); *A61K 8/97* (2013.01); *A61Q 3/02* (2013.01); *A61K 2800/43* (2013.01); *A61K 2800/49* (2013.01); *A61K 2800/594* (2013.01); *A61K 2800/87* (2013.01); *A61K 2800/95* (2013.01)

(58) Field of Classification Search
CPC .................................... A45D 34/045
USPC .................................. 401/121–129
See application file for complete search history.

(56) References Cited

U.S. PATENT DOCUMENTS

| | | | |
|---|---|---|---|
| 6,939,551 B2 | 9/2005 | Amato et al. | |
| 7,465,113 B2 * | 12/2008 | Gueret | A46B 9/021 15/168 |
| 8,790,669 B2 | 7/2014 | Li et al. | |

* cited by examiner

*Primary Examiner* — David P Angwin
*Assistant Examiner* — Joshua R Wiljanen
(74) *Attorney, Agent, or Firm* — Oblon, McClelland, Maier & Neustadt, L.L.P.

(57) ABSTRACT

A nail care system containing (1) at least one composition containing at least one adhesive agent, at least one primary film former and at least one plasticizer; and (2) an applicator is provided.

13 Claims, 2 Drawing Sheets

NAIL CARE SYSTEM

CROSS-REFERENCE TO RELATED APPLICATIONS

This application is a continuation of and claims the benefit of priority under 35 U.S.C. § 120 from U.S. application Ser. No. 14/931,400, filed Nov. 3, 2015, now allowed, the entire contents of which are incorporated herein by reference.

FIELD OF THE INVENTION

The present invention relates to a nail care system comprising (1) a composition comprising at least one adhesive agent, at least one primary film forming polymer, and at least one plasticizer; and (2) an applicator.

DISCUSSION OF THE BACKGROUND

Traditional nail polish products contain a large amount of cellulose based polymers such as nitrocellulose, primarily because cellulose based polymers provide good adhesion of the compositions to nails upon application. Although nitrocellulose is the preferred adhesive agent for use in nail polish compositions and it constitutes the "gold standard" of adhesive agents in nail polish compositions, the traditional nail compositions containing nitrocellulose are generally known for poor long wear characteristics. The use of low levels of nitrocellulose tends to result in the coated films being easily damaged. On the other hand, the use of high levels of nitrocellulose results in the nail polishes being too hard and inflexible. Further, nitrocellulose does not impart high gloss.

In the past, proposed solutions to improve adhesion and gloss included incorporating into compositions containing nitrocellulose high levels of plasticizers and replacing nitrocellulose with other alternative materials. For instance, U.S. Pat. No. 6,939,551 relates to the use of nitrocellulose in the presence of butyl phthalimide isopropyl phthalimide, and U.S. Pat. No. 8,790,669 discloses the use of latex film formers instead of nitrocellulose.

Despite such attempts, there remains a need for nail compositions which adhere, are glossy and have long wear properties and applicators for applying such compositions to nails.

SUMMARY OF THE INVENTION

The present invention relates to a nail care system comprising:
(a) at least one composition comprising:
  (1) at least one adhesive agent;
  (2) at least one primary film former; and
  (3) at least one plasticizer; and
(b) at least one applicator. Preferably, the applicator comprises:
  a gripping portion;
  a stem extending from the gripping portion along a longitudinal axis X-X, the stem having, along the axis X-X, a succession of noncircular cross sections that are angularly offset with respect to one another about the axis X-X so as to form a helical pattern, and
  an applicator member fixed in a housing at the free end of the stem,
  the applicator being characterized in that the sections of the succession of noncircular cross sections comprise a concavity so as to form a helical groove around the stem, or a protuberance so as to form a helical rib around the stem, the groove or the rib having a gradient of between 10° and 70° with respect to an axis perpendicular to the axis X-X, or in that the stem comprises a succession of flattened cross sections, the stem comprising a twisted portion about the longitudinal axis X-X.

The present invention also relates to a nail care system comprising:
(a) at least one composition comprising:
  (1) at least one adhesive agent;
  (2) at least one primary film former; and
  (3) at least one plasticizer, and
further comprising at least one co-film former, and at least one solvent. Optionally, the composition further comprises at least one secondary film former, at least one pigment, at least one thixotropic agent, at least one silicone acrylate copolymer and/or at least one additive; and
(b) at least one applicator. Preferably, the applicator comprises:
  a gripping portion;
  a stem extending from the gripping portion along a longitudinal axis X-X, the stem having, along the axis X-X, a succession of noncircular cross sections that are angularly offset with respect to one another about the axis X-X so as to form a helical pattern, and
  an applicator member fixed in a housing at the free end of the stem,
  the applicator being characterized in that the sections of the succession of noncircular cross sections comprise a concavity so as to form a helical groove around the stem, or a protuberance so as to form a helical rib around the stem, the groove or the rib having a gradient of between 10° and 70° with respect to an axis perpendicular to the axis X-X, or in that the stem comprises a succession of flattened cross sections, the stem comprising a twisted portion about the longitudinal axis X-X.

The present invention further relates to the above nail care systems, wherein the at least one composition is in the form of a base coat, a color coat or a top coat.

The present invention also relates to a kit for a nail care system comprising (1) at least one composition as described above; and (2) at least one applicator.

The present invention also relates to methods for making up and/or protecting nails comprising applying to the nails a composition of the present invention using an applicator of the present invention.

It is to be understood that both the foregoing general description and the following detailed description are exemplary and explanatory only, and are not restrictive of the invention.

BRIEF DESCRIPTION OF THE DRAWINGS

FIG. 1 is a schematic view, in axial section, of a device for applying a product to the nails, FIG. 2 partially shows the applicator of the device from FIG. 1, FIG. 3 shows the stem of the applicator from FIG. 1 on its own, in axial section, FIG. 4 shows a detail of the housing that holds the bristles of the brush, FIG. 5 is a cross section on V-V in FIG. 4.

DETAILED DESCRIPTION OF THE INVENTION

In the following description of the invention and the claims appended hereto, it is to be understood that the terms used have their ordinary and accustomed meanings in the art, unless otherwise specified.

"About" as used herein means within 10% of the indicated number (e.g. "about 10%" means 9%-11% and "about 2%" means 1.80-2.2%).

"A" or "an" as used herein means "at least one."

As used herein, all ranges provided are meant to include every specific range within, and combination of subranges between, the given ranges. Thus, a range from 1-5, includes specifically 1, 2, 3, 4 and 5, as well as subranges such as and 2-5, 3-5, 2-3, 2-4, 1-4, etc.

"Adhesion" as used herein, refers to chemical and/or physical bonding between a coating and a substrate. Good adhesion between nail polish and nail surface should translate to good wear properties on consumers.

"Adhesive agent" or "adhesive" means a polymer that improves chemical and/or physical bonding between a coating and a substrate. In this invention, the adhesive agent improves bonding between compositions and the nail surface or other compositions.

"Young's modulus" as used herein, means a force per unit area (MPa) that is needed to stretch a sample material. It is defined as the slope of stress-strain curve at the elastic region where the deformation of the sample can be restored to its original state. Stress is the force causing deformation divided by the area to which the force is applied and the strain is the deformation ratio in length to its original state. The high value of Young's modulus means that the material is hard and stiff, on the contrary low value means that the material is soft, flexible and more ductile.

"Removal" or "Easy removal" means the composition may be substantially removed with acetone or other organic solvents not limited to butyl acetate, isopropyl alcohol, ethanol, ethyl acetate, methyl acetate, methyl ethyl ketone, and mixtures thereof.

"Impact resistance" as used herein, means minimum of energy to cause failure (deformation, cracking) of the tested material. The impact energy depends on the weight used to damage a sample and the height from which the weight is dropped. Higher the weight and height from which the weight is dropped, higher is the impact energy. The impact resistance values are given in kg·cm and correspond to the lowest value of (weight×height) for which the specimen shows failure. A drop weight impact tester was used. The dynamic energy (expressed in Joule (J)) in a falling object at the impact moment can be calculated as:

$$E = F_w h = mgh, \text{ wherein}$$

$F_w$=force due to gravity–weight (N, $lb_f$)
g=acceleration of gravity (9.81 m/s$^2$, 32.17405 ft/s$^2$)
h=falling height (m)

The equation can be combined with the equation of work:

$$F = mgh/s$$

s=distance

"Abrasion resistance" as used herein, means resistant to disruptions caused by being exposed to rough materials.

"Film former", "film-forming polymer" or "film forming agent" or "co-film former" as used herein means a polymer or resin that leaves a film on the substrate to which it is applied, for example, after a solvent accompanying the film former has evaporated, absorbed into and/or dissipated on the substrate.

"Free" or "devoid" of as it is used herein means that while it is preferred that no amount of the specific component be present in the composition, it is possible to have very small amounts of it in the compositions of the invention provided that these amounts do not materially affect at least one, preferably most, of the advantageous properties of the compositions of the invention. Thus, for example, "free of solvents" means that non-aqueous solvents are preferably omitted (that is 0% by weight), but can be present in the composition at an amount of less than about 0.25% by weight, typically less than about 0.1% by weight, typically less than about 0.05° by weight, based on the total weight of the composition.

"Water free" or "free of water" herein means that water is preferably omitted (that is 0% by weight), but can be present in the composition at an amount of less than about 0.25% by weight, typically less than about 0.1% by weight, typically less than about 0.05% by weight, based on the total weight of the composition.

"Glass transition temperature" (Tg) means the temperature at which the amorphous material changes from a glassy solid state to a rubbery state. This temperature may be measured by standard techniques in the art, such as DSC (Differential Scanning calorimeter), e.g., according to the ASTM D3418-97 standard.

"Makeup Result" as used herein, refers to compositions where color remains the same or substantially the same as at the time of application, as viewed by the naked eye, after an extended period of time. "Makeup Result" may be evaluated by evaluating long wear properties by any method known in the art for evaluating such properties. For example, long wear may be evaluated by a test involving the application of a composition to nails and evaluating the color of the composition after an extended period of time. For example, the color of a composition may be evaluated immediately following application to nails and these characteristics may then be re-evaluated and compared after a certain amount of time. Further, these characteristics may be evaluated with respect to other compositions, such as commercially available compositions.

"Making up" as used herein means to provide decoration (for example, color) to the nail. "Protecting" as used herein means to inhibit damage to the nail (for example, chipping) by providing a protective layer on the nail.

"Nails", "fingernail or "toenail" refers to a human keratinous substrate on a finger or toe which can be treated (decorated) with a single or multiple nail cosmetic compositions.

"Nail treatment system" means multiple compositions applied on the surface of nails.

"Nail composition" or "lacquer" or "nail polish" or "nail enamel" or "nail coating" or "nail film" refers to nail enamel usable as a basecoat, color coat, top coat, clear coat and protective coat applied on nails separately and/or as a combined application of the above.

"Substituted" as used herein, means comprising at least one substituent. Non-limiting examples of substituents for substitution include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Shine" or "gloss" as used herein, refers to surface shininess. Gloss meters are commonly used in the nail polish art as well as in other areas of cosmetics, and measure the amount of light reflected from the surface or film of interest. The gloss may be Quantified, for example, as a % reflectance at 20°.

"Shine enhancing agent" or "shine increasing agent" in accordance with present invention means increasing shine or, as the case may be, mitigating or reducing any reduction in shine that may result from the use of corresponding amounts of non-shine enhancing materials.

"Hardness" as used herein, means how resistant a material is to various kinds of permanent shape change when a force is applied. The force can be measured and quantified as described ahead in this application.

"Water resistance" as used herein, means resistance of a material (substance) to the penetration of water, which may cause degradation of that material. The method implemented if assessment of this invention is further disclosed "The acid number" or "the acid value" means the quantity of base, expressed in milligrams of potassium hydroxide, that is required to neutralize the acidic constituents in 1 g of sample. It allows to quantify the amount of acid present in the sample.

"Polymer or copolymer having a high acid value (number)" means polymer or copolymer which requires a high amount (in milligrams) of potassium hydroxide (KOH) to neutralize the acid that is present in one gram of a sample of the polymer (i.e., mg KOH/gram).

The compositions and methods of the present invention can comprise, consist of, or consist essentially of the essential elements and limitations of the invention described herein, as well as any additional or optional ingredients, components, or limitations described herein or otherwise useful.

Referred to herein are trade names for materials including, but not limited to polymers and optional components. The inventors herein do not intend to be limited by materials described and referenced by a certain trade name. Equivalent materials (e.g., those obtained from a different source under a different name or catalog (reference) number) to those referenced by trade name may be substituted and utilized in the methods described and claimed herein.

All percentages and ratios are calculated by weight unless otherwise indicated. All percentages are calculated based on the total weight of a composition unless otherwise indicated. All component or composition levels are in reference to the active level of that component or composition, and are exclusive of impurities, for example, residual solvents or by-products, which may be present in commercially available sources.

Applicator

In accordance with the present invention, an applicator for applying a nail composition to nails is provided. Preferably, the applicator is one as disclosed in WO2015/0019029 (PCT/FR2014/052063), the entire contents of which is herein incorporated by reference.

According to preferred embodiments, the applicator comprises a gripping portion, a stem extending from the gripping portion along a longitudinal axis X-X, and an applicator member fixed in a housing at the free end of the stem. The stem has, along the axis X-X, a succession of noncircular cross sections that are angularly offset with respect to one another about said axis X-X so as to form a helical pattern.

The sections of the succession of noncircular cross sections may comprise a concavity so as to form a helical groove around the stem.

The sections of the succession of noncircular cross sections may comprise a protuberance so as to form a helical rib around the stem.

The sections of the succession of noncircular cross sections may be approximately circular outside the portion comprising said protuberance or said concavity.

The groove or the rib may have a gradient of between 10° and 70°, and in particular greater than or equal to 45°, with respect to an axis perpendicular to the axis X-X.

All of the sections of the succession of noncircular cross sections may be identical.

The applicator member may be a tuft of bristles fixed in the housing. The length of the portion of the bristles that extends outside the housing may then be between 5 and 20 mm.

The applicator member may be an end piece made of thermoplastic material.

The succession of noncircular cross sections may extend over more than half the height of the stem.

The succession of noncircular cross sections may extend as far as the free end of the stem.

The largest dimension of the opening in the housing, measured perpendicularly to the axis X-X, may be less than or equal to 5 mm, or even less than or equal to 3 mm.

The largest transverse dimension of a section of the stem may be less than or equal to 5 mm.

The stem may be produced in one piece with the gripping member by molding thermoplastic material.

The invention system also relates to a device for packaging and applying a cosmetic product, comprising a container containing the product to be applied and an applicator as defined above.

Figures 1, 2, 3, 4, 5:
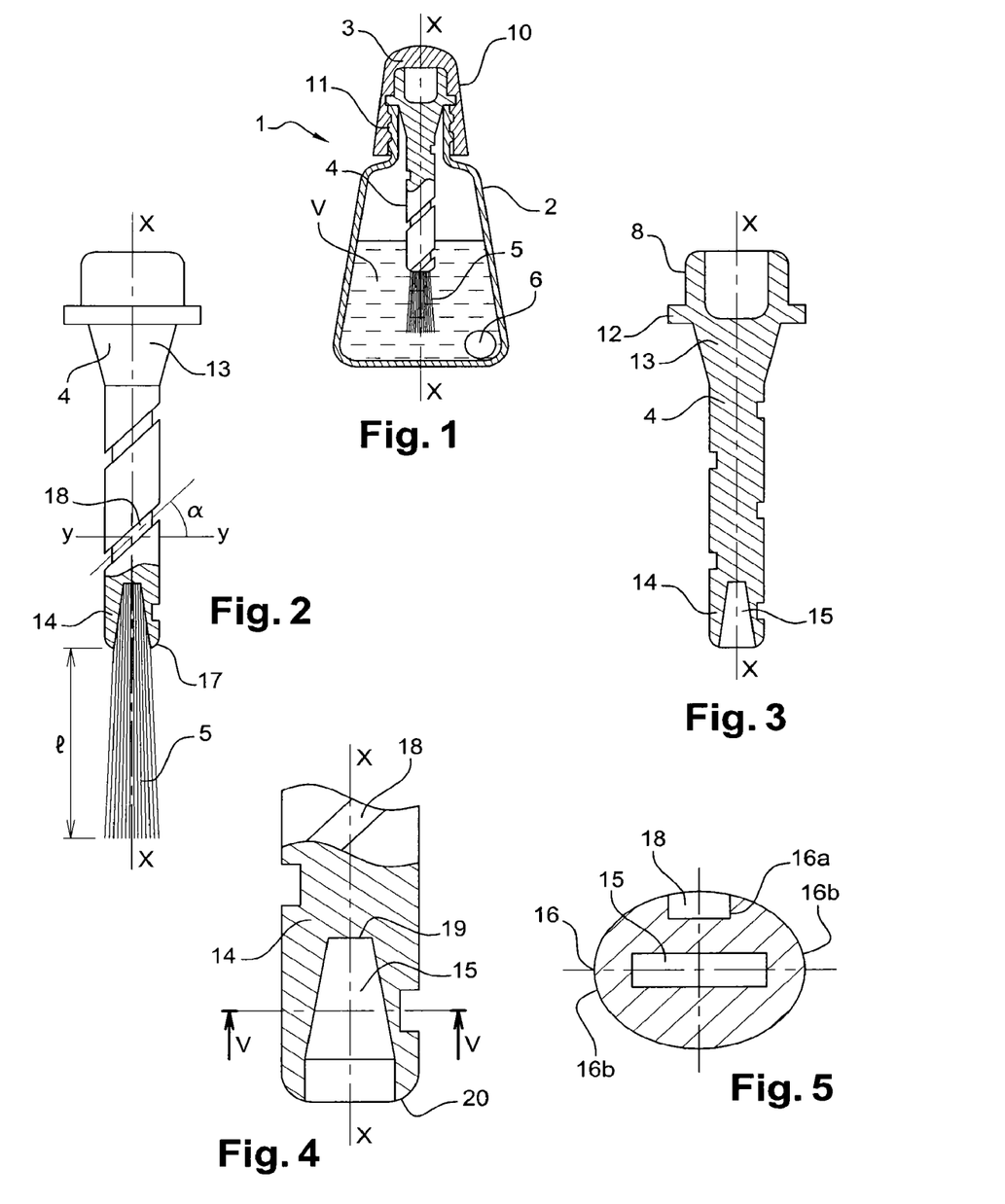

The applicator may be better understood from reading the following detailed description of nonlimiting illustrative embodiments thereof and from examining the appended drawing, in which:

FIG. 1 shows a device 1 for applying a composition of the present invention (v) to the nails. This device comprises a container 2 containing the composition (V) and an applicator 3. The applicator comprises a plastics stem 4 extending along a longitudinal axis X-X, said stem being provided at one end with an applicator member formed by a brush 5 and at the other end with a gripping member 10 that likewise constitutes a cap for closing the container 2.

In a variant that is not shown, other types of applicator member can also be suitable, for example, but in a nonlimiting manner, the applicator member may be an end piece made of thermoplastic material or foam.

The applicator member may also be flocked.

The container 2 comprises an opening defined by a neck of the container 2. Preferably, the container 2 does not have a means for wiping the applicator member when the latter is withdrawn from the container 2.

The container may comprise a ball 6, for example a metal ball, for homogenizing the composition V before application by shaking the device 1.

The container may be transparent or translucent. To this end, it may be made of glass.

Referring to FIGS. 2 to 5, it can be seen that the stem 4 comprises at its upper end a skirt 8 for fixing it in the closure cap 10. In a variant that is not shown, the stem may be produced in one piece with the closure cap of the container by molding plastic material.

The closure cap 10 is configured to be screw-fastened or snap-fastened on the neck 11 of the container 2.

Under the flange 12, the stem 4 comprises a conical part 13 that can help to seal the closure of the container 2 when the applicator 3 is in place on the latter. Sealing could also be obtained by interaction of surfaces of the cap 10 and of the neck 11 of the container 2.

The stem extends in an approximately rectilinear manner along the axis X-X from its conical part 13 to its free end 17. The largest transverse dimension of that portion of the stem that is dipped in the product contained in the container when the applicator is in place thereon can then be less than or equal to 5 mm.

The stem 4 also comprises a lower end portion 14 which is provided with a housing 15 for fixing the applicator member. In the example shown, the housing 15 receives a portion of the bristles of the brush 5, which are fixed for example by stapling, adhesive bonding, fusion or overmolding.

The opening in the housing 15 intersects the longitudinal axis X-X of the stem 4. Advantageously, the opening is perpendicular to this longitudinal axis X-X. The housing 15 may have any kind of cross section, for example a circular or polygonal cross section. Advantageously, the housing 15 has an opening with a rectangular or oblong cross section, having an elongate shape along an axis perpendicular to the longitudinal axis X-X of the stem 4, thereby making it possible to obtain a substantially homogeneous distribution of the bristles.

Figures 7, 10, 11, 12, 13, 14, 15, 16:
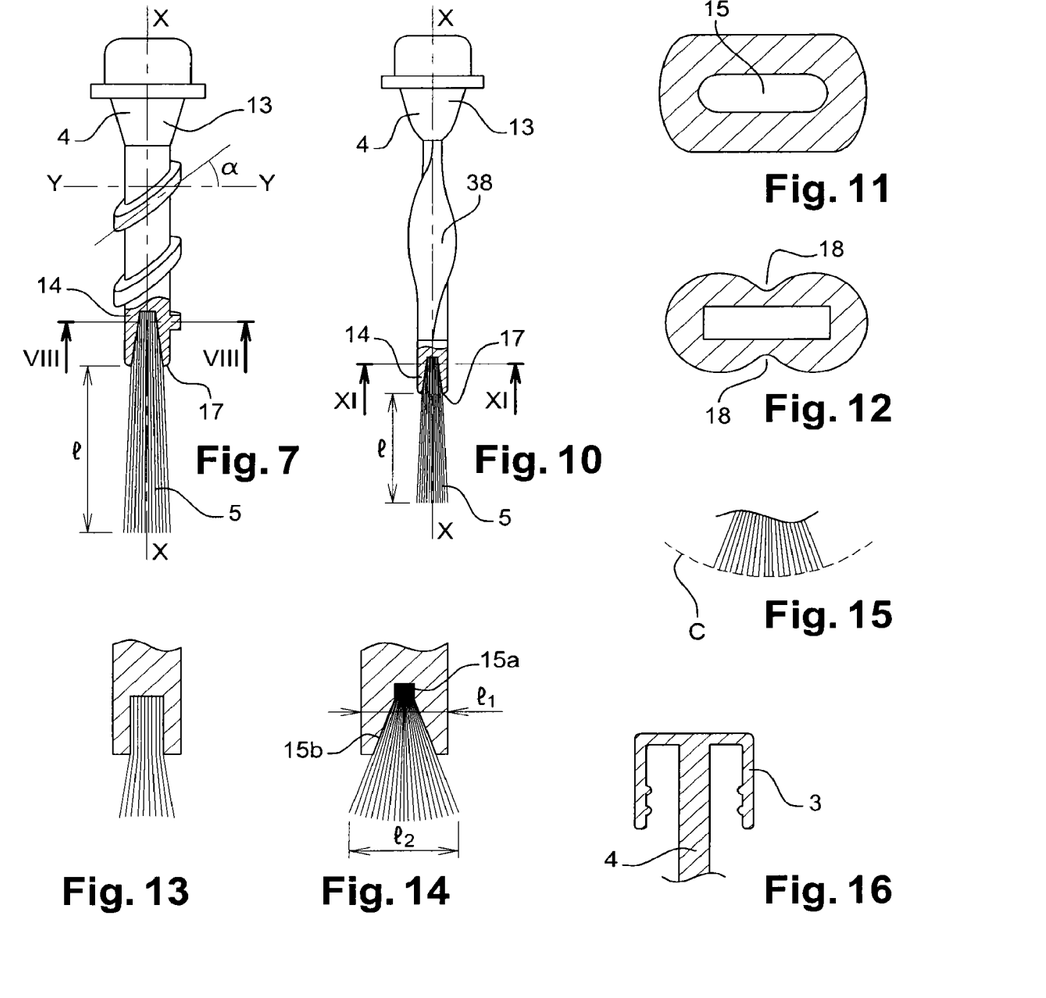
FIG. 7 shows a second embodiment of the stem of the applicator of the invention.
FIG. 10 shows a third embodiment of the stem of the applicator of the invention.
FIG. 11 is a cross section on XI-XI in FIG. 10.
FIG. 12 shows a variant embodiment of the stem from FIG. 10 in section on XI-XI.
FIGS. 13 and 14 illustrate two configurations of the housing, corresponding to different distributions of the bristles on the outside of the stem.
FIG. 15 shows an end portion of the bristles of the brush on its own.
FIG. 16 is a partial longitudinal section through the stem and through a cap produced in one piece therewith.

As can be seen in FIG. 4, the housing 15 may have a cross section that decreases in size toward the bottom 19 of the housing. This decrease in size can be realized in accordance with the desired divergence for the bristles. Depending on the shape given to the housing 15, a more or less wide bundle of bristles can be obtained, as illustrated in FIGS. 13 and 14. FIG. 13 shows that by giving the housing 15 a substantially constant cross section, a brush in which the bristles are relatively tight is obtained, whereas by giving the housing 15 an outwardly divergent shape, the bristles are allowed to become increasingly spaced apart from one another so as to form a relatively wide bundle, as in FIG. 14.

The housing 15 may be produced with an indentation 15a in its base, the bristles being fixed to the stem in said indentation 15a. This indentation can open out onto a part 15b that flares in the direction of the opening in the housing 15, allowing the bristles to become spaced apart from one another so as to give the brush a widened shape and so that the bristles of the brush 5 are spaced apart when the brush is applied to the nail.

The housing 15 can then be produced such that the maximum transverse dimension 12 of the brush, measured perpendicularly to the axis X-X, is greater than the transverse dimension 11 of the stem at the housing 15, as can be seen in FIG. 14.

In particular, the housing can be arranged such that the bristles extend on the outside of the housing over a width, measured perpendicularly to the axis X-X, greater than the width of the stem at the housing. A relatively wide brush is then obtained.

The length of the portion of the bristles that extends outside the housing 15 in the stem is between 5 and 20 mm, for example.

The free ends of the bristles of the brush 5 may be situated, for example, as can be seen in FIG. 15, along an approximately circular curve C. Thus, the free ends of the bristles can describe more or less an arc of a circle, having a radius of curvature of between 2 and 15 mm for example, in particular between 4 and 10 mm. In a variant, the free ends of the bristles could be situated substantially along a straight line, for example.

The largest dimension of the opening in the housing, measured perpendicularly to the axis X-X, may be less than or equal to 2 mm.

The free end 17 of the stem 4 may comprises a chamfer 20, as can be seen in FIG. 4.

In the example illustrated in FIGS. 1 to 6, the stem 4 comprises a groove 18 along the major part of its length as far as its distal end 17. This groove 18 extends along and around the stem 4 so as to form a helical spiral. Thus, the stem 4 has, along the axis X-X, a succession of noncircular cross sections that are angularly offset with respect to one another about said axis X-X so as to form a pattern in the form of a helical groove 18. More specifically, the stem 4 has a succession of sections in which the external contour comprises a convex circular part 16b joining the edges of a concavity 16a defining the groove 18.

Figure 6:
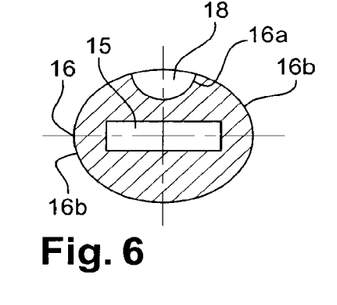
FIG. 6 shows a variant embodiment of the stem from FIG. 4 in section on V-V.

The concavity can have a polygonal profile, as in FIG. 5, or simply a profile in the form of a concave arc of a circle, as in FIG. 6.

This groove 18 may extend over more than half the height of the stem 4. Said groove 18 extends preferably from the distal end 17 of the stem 4 so as to lead onto the applicator member.

The groove has a gradient of between 10° and 70° with respect to an axis Y-Y perpendicular to the axis X-X. Advantageously, the gradient is greater than or equal to 45° with respect to an axis Y-Y perpendicular to the axis X-X. The gradient is in particular adapted to the viscosity of the product so as to obtain a flow rate suitable for the desired use.

The stem may also comprise a plurality of grooves that may or may not cross one another.

Figure 8:
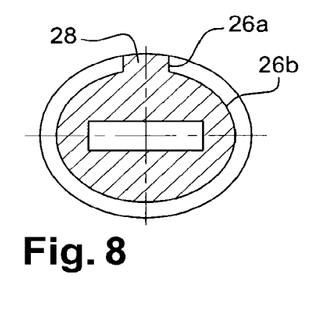
FIG. 8 is a cross section on VIII-VIII in FIG. 7.
Figure 9:
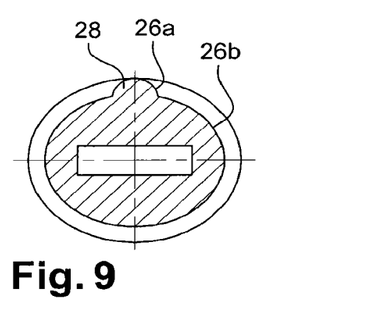
FIG. 9 shows a variant embodiment of the stem from FIG. 7 in section on VIII-VIII.

In a variant shown in FIGS. 7 to 9, the stem comprises a rib 28 extending along and around the stem so as to form a helical rib. Thus, the stem has, along the axis X-X, a succession of noncircular cross sections that are angularly offset with respect to one another about said axis X-X so as to form a pattern in the form of a helical rib 28. More specifically, the stem 4 has a succession of sections in which the external contour comprises a convex circular part 26b joining the edges of a convex protuberance 26a.

The protuberance can have a polygonal profile, as in FIG. 8, or simply a profile in the form of a concave arc of a circle, as in FIG. 9.

This rib 28 may extend over more than half the height of the stem 4. Said rib extends preferably from the distal end 17 of the stem 4.

The rib 28 has a gradient of between 10° and 70° with respect to an axis Y-Y perpendicular to the axis X-X. Advantageously, the gradient is greater than or equal to 45° with respect to an axis Y-Y perpendicular to the axis X-X.

In a variant shown in FIGS. 10 to 12, the stem comprises a flattened cross section, and more particularly a succession of flattened cross sections, and said stem 4 comprises a twisted portion 38 about the longitudinal axis X-X. Thus, the stem has, along the axis X-X, a succession of flattened, i.e. noncircular, cross sections that are angularly offset with respect to one another about said axis X-X so as to form a helical pattern.

More specifically, the stem 4 has a succession of noncircular sections, for example rectangular or oblong sections, as in FIG. 11, or flattened sections having a protuberance or concavity, as in FIG. 12.

The noncircular cross sections of the succession may be identical or vary in a progressive manner.

The twisted portion 38 may extend over more than half the height of the stem 4 and extend as far as the distal end 17 of the stem 4, or not.

The angular offset forming the twist may be between a quarter turn and 6 turns. The twist may extend along a length of between 10 mm and 70 mm.

Advantageously, the twisted portion 38 stops at the bottom 19 of the housing 15 in order to have a nontwisted housing.

The device 1 is used in the following manner.

The user agitates the container 2 to allow the ball 6 to homogenize the composition of the present invention (V) and then the user unscrews the cap 10 and uses the brush 5 to apply the product.

When the applicator 3 is withdrawn from the container 2, product is present on the stem 4 and flows by gravity in the direction of the brush 5. The product thickness is greater at the grooves 18, which can retain more product.

The product flows along the helical pattern, and thus more slowly than if it were to flow axially along the stem. This makes it possible to apply the product more easily and more precisely without having to reload the brush by replacing it in the container.

The applicator is not limited to the examples illustrated. The features of the various examples can in particular be combined as parts of variants which are not illustrated.

Thus, it is also possible to have a plurality of grooves or ribs with identical or different shapes on one and the same stem. Similarly, a stem can comprise both a groove and a rib.

Nail Composition

In accordance with the present invention, nail compositions comprising: at least one adhesive agent; at least one primary film former; and at least one plasticizer are provided.

According to these preferred embodiments, the weight ratio of at least one primary film former to at least one plasticizer is greater than or equal to about 1:1, preferably between about 1:2 and about 1:20, preferably between about 1:2 and about 1:15, and preferably between about 1:2 and about 1:10, by weight, relative to the total weight of the composition, including all ranges and subranges therebetween.

According to these preferred embodiments, the weight ratio of at least one adhesive agent to at least one primary film former is greater than or equal to about 1:1, preferably between about 25:1 and about 2:1, preferably between about 20:1 and about 2:1, and preferably between about 15:1 and about 2:1, by weight, relative to the total weight of the composition, including all ranges and subranges therebetween.

In accordance with the present invention, nail compositions comprising: at least one adhesive agent; at least one primary film former; at least one co-film former; at least one plasticizer; and at least one solvent are provided.

According to these preferred embodiments, the weight ratio of at least one primary film former to at least one plasticizer is greater than or equal to about 1:1, preferably between about 1:2 and about 1:20, preferably between about 1:2 and about 1:15, and preferably between about 1:2 and about 1:10, by weight, relative to the total weight of the composition, including all ranges and subranges therebetween.

According to these preferred embodiments, the weight ratio of at least one adhesive agent to at least one primary film former is greater than or equal to about 1:1, preferably between about 25:1 and about 2:1, preferably between about 20:1 and about 2:1, and preferably between about 15:1 and about 2:1, by weight, relative to the total weight of the composition, including all ranges and subranges therebetween.

According to preferred embodiments, any of the above embodiments optionally may contain at least one thixotropic agent, at least one secondary film former, at least one silicone acrylate copolymer, at least one pigment; and/or at least one additive.

In accordance with the present invention, nail compositions comprising: at least one adhesive agent; at least one primary film former; at least one co-film former; at least one plasticizer; at least one silicone acrylate copolymer and at least one solvent are provided.

According to these preferred embodiments, the weight ratio of at least one primary film former to at least one plasticizer is greater than or equal to about 1:1, preferably between about 1:2 and about 1:20, preferably between about 1:2 and about 1:15, and preferably between about 1:2 and about 1:10, by weight, relative to the total weight of the composition, including all ranges and subranges therebetween.

According to these preferred embodiments, the weight ratio of at least one adhesive agent to at least one primary film former is greater than or equal to about 1:1, preferably between about 25:1 and about 2:1, preferably between about 20:1 and about 2:1, and preferably between about 15:1 and about 2:1, by weight, relative to the total weight of the composition, including all ranges and subranges therebetween.

According to these preferred embodiments, the weight ratio of at least one primary film former to the at least one silicone acrylate copolymer is greater than or equal to about 1:1, preferably between about 20:1 and about 1.5:1, preferably between about 17:1 and about 1.5:1, and preferably between about 15:1 and about 2:1, by weight, relative to the total weight of the composition, including all ranges and subranges therebetween.

According to preferred embodiments of the present invention, nail compositions (as described above) having shine (gloss) greater than about 60 GU (Gloss Units) measured at 20° angle are provided.

In accordance with the present invention, the nail compositions can be a base coat, a color coat or a top coat. However, it should be understood that each coat in the nail composition, itself, can comprise one or more layers. Thus, for example, the at least one color coat can comprise one or more color coat layers; the at least top coat can comprise one or more top coat layers; the at least one base coat can comprise one or more base coat layers. Preferably, each basecoat, color coat and topcoat compositions contain three or fewer layers of compositions, preferably two or fewer layers of compositions, and preferably a single layer of compositions.

During application of the nail composition, the base coat is typically applied directly to the nail, the color coat is typically applied either directly to the nail or to a base coat, and the top coat is typically applied to a color coat.

The nail compositions of the present invention display very strong adhesion to the nail, good wear, resistance to damage and superb gloss.

Without being bound by theory, it is believed that adhesive agent, primary film forming polymers and plasticizer present in the inventive compositions improve adhesion of the inventive nail compositions. In addition, when it is a color coat, the inventive color coat is characterized by low Young's modulus value which means that the color coat is flexible. On the other hand, when it is a top coat, Young's modulus values of the inventive top coat are higher, which is typical for hard materials. The unique combination of properties of the invention compositions deliver nail compositions which consumers can wear with minimal or no damage for an extended period (for example at least 7 to 10 days). In addition, when it is a color coat or top coat, exceptional gloss of the inventive color coat and top coat does not decrease significantly during the time of wearing.

Owing to the unique architecture of compositions of the present invention, when it is a color coat, it is characterized by shine (gloss), good flexibility and ductility (low hardness and low Young's modulus values), good water resistance and adhesion. When it is a top coat, the top coat is categorized by being relatively stiff (higher Young's modulus values), having a good water resistance and high resistance to abrasion. The top coat also has an excellent shine, which can be equal or higher than shine of the color coat.

Color Coat

According to preferred embodiments, a composition of the present invention may be a color coat.

Preferably, a color coat composition of the present invention has one or more of the following properties:

Shine (gloss) greater than about 60 GU (Gloss Units) measured at 20° angle, preferably greater than about 70 GU, preferably greater than about 75 GU;

Persoz pendulum hardness lower than about 35 oscillations, preferably lower than about 30 oscillations, preferably lower than about 25 oscillations; and Young's modulus values lower than about 45 MPa, preferably lower than about 40 MPa, preferably lower than about 35 MPa.

Preferably, a color coat composition of the present invention has a weight ratio of secondary film former to plasticizer which is greater than or equal to 1:1, by weight, relative to the total weight of the composition, preferably greater than 2:1 and preferably greater than 2.5:1.

Preferably, a color coat composition of the present invention has a weight ratio of at least one adhesive agent to at least one primary film forming polymer between about 10:1 and about 1:1, preferably between about 5:1 and about 2:1, by weight, relative to the total weight of the composition, including all ranges and subranges therebetween.

Top Coat

According to preferred embodiments, a composition of the present invention may be a top coat.

Preferably, a top coat composition of the present invention has one or more of the following properties:

Shine (gloss) greater than about 70 Gloss Units (GU) measured at 20° angle, preferably greater than 75 GU, preferably greater than 80 GU;

Young's modulus values lower than about 1200 MPa, preferably lower than about 1100 MPa, preferably lower than about 1000 MPa.

Preferably, a topcoat is clear and/or transparent. As used herein, the term "transparent" refers to that the composition has a HAZEBYK index of less than 5 as measured with a KYKHAZEGLOSS type gloss meter.

Preferably, a top coat composition of the present invention has a weight ratio of at least one primary film former to at least one plasticizer from about 0.5 to about 10, preferably from about 0.5 to about 4, by weight, relative to the total weight of the composition, including all ranges and subranges therebetween.

Adhesive Agent

In accordance with the present invention, nail compositions comprising at least one adhesive agent are provided. Preferably, the adhesive agent is chosen from the group consisting of radical or polycondensate type synthetic polymers, polymers of natural origin, and mixtures thereof.

Preferably, the adhesive agent is chosen from polysaccharide derivatives, such as cellulose or guar gum derivatives. Preferred polysaccharide derivatives include nitrocellulose or a polysaccharide ester or alkylether. The term "polysaccharide ester or alkylether" refers to a polysaccharide consisting of repeat units comprising at least two identical or different rings and having a degree of substitution per saccharide unit between 1.9 and 3, preferably between 2.2 and 2.9, and more particularly between 2.4 and 2.8. The term substitution refers to the functionalization of hydroxyl groups into ester and/or alkylether functions, and/or the functionalization of carboxyl groups into ester functions. In other words, it may consist of a polysaccharide, partially or totally substituted with ester and/or alkylether groups. Preferably, the hydroxyl groups may be substituted with $C_2$-$C_4$ ester and/or alkylether functions.

Particular mention may be made of cellulose esters (such as cellulose acetobutyrates or cellulose acetopropionates), cellulose alkylethers (such as ethylcelluloses), and ethylguars.

Preferably, the at least one adhesive agent is present in the nail compositions of the present invention at a total content greater than or equal to 0.1%, preferably from about 0.2% to about 25%, preferably from about 1% to about 20%, preferentially from about 3% to about 18%, by weight in relation to the total weight of the composition.

Plasticizers

In accordance with the present invention, nail compositions comprising at least one plasticizer are provided. Generally speaking, plasticizers are additives used to optimize the mechanical properties of films. They tend to reduce the Glass Transition Temperature (Tg) and increase the softness and flexibility of the films.

Preferably, suitable plasticizers have a boiling point measured at ambient pressure of less than or equal to 285° C., preferably less than or equal to 270° C., and preferably less than or equal to 250° C. In the present specification, the boiling point values are to be considered accurate to ±2° C. owing to the uncertainties of boiling point measurement.

Any plasticizing agent typically found in nail polish compositions can be used. Examples of suitable plasticizers include, but are not limited to, glycols and their ester derivatives, esters of acids, in particular carboxylic acids, such as citrates, adipates, carbonates, tartrates, phosphates or sebacates, oxyethylenated derivatives, such as oxyethylenated oils, and their mixtures. For example, suitable plasticizing agents include, but are not limited to, diisobutyl adipate, the ester of teributyl acid and 2,2,4-trimethylpentane-1,3-diol, diethyl adipate, diethyl phthalate, dibutyl phthalate, dioctyl phthalate, butyl 2-ethylhexyl phthalate, dimethyl sebacate, dibutyl sebacate, ethyl stearate, 2-ethylhexyl palmitate, dipropylene glycol n-butyl ether, tributyl phosphate, tributoxyethyl phosphate, tricresyl phosphate, triphenyl phosphate, glycerol triacetate, butyl stearate, butyl glycolate, benzyl benzoate, butyl acetyltricinoleate, glyceryl acetyltricinoleate, dibutyl phthalate, diisobutyl phthalate, dioctyl phthalate, dimethoxyethyl phthalate, diamyl phthalate, triethyl citrate, tributyl citrate, tributyl acetylcitrate, tri(2-ethylhexyl) acetylcitrate, dibutyl tartrate, camphor, ethyl tosylamide and mixtures thereof.

Preferably, the plasticizer is preferably present in the composition in an amount from about 0.1% to about 25% by weight, preferably from about 0.5% to about 20% by weight, preferably from about 1% to about 10% by weight, of the total weight of the composition, including all ranges and subranges there between.

Primary Film Forming Polymer

In accordance with the present invention, nail compositions comprising at least one primary film forming agent are provided. Preferred examples of primary film former agents include but are not limited to acrylic polymers (homopolymers or copolymers), preferably in the form of solid powders (flakes) and solvent free. Specific examples of suitable primary film formers include:

Synthetic polymers of the polycondensate type or of the free-radical type;

Acrylic polymers resulting from the copolymerization of monomers chosen from the esters and/or amides of acrylic acid and/or of methacrylic acid. As examples of monomers of ester type, mention may be made of methyl methacrylate, ethyl methacrylate, butyl methacrylate, isobutyl methacrylate, 2-ethylhexyl methacrylate and lauryl methacrylate. As examples of monomers of amide type, mention may be made of N-t-butylacrylamide and N-t-octylacrylamide; and Acrylic polymers obtained by copolymerization of ethylenically unsaturated monomers containing hydrophilic groups, preferably of nonionic nature, such as hydroxyethyl acrylate, 2-hydroxypropyl acrylate, hydroxyethyl methacrylate and 2-hydroxypropyl methacrylate.

Generally speaking, the primary film-forming polymers may be chosen from synthetic polymers such as polyurethanes, acrylic polymers, styrene acrylate copolymers, acrylate silicone copolymers, vinyl polymers, polyvinylbutyrals, alkyd resins, ketone/aldehyde resins, and resins from aldehyde condensation products, such as aryl sulfonamide formaldehyde resins such as toluene or sulfonamide formaldehyde resin.

According to particularly preferred embodiments of the invention, the primary film forming agent is selected from carboxyl functional acrylate polymers having a moderate to high glass transmission temperature (Tg) value. The "moderate to high glass transmission" as used in the context of the present invention, refers to an acrylates copolymer having Tg value ranging from about 40° C. to about 95° C., more preferably from about 60° C. to about 90° C., and more preferably from about 70° C. to about 85° C.

According to preferred embodiments, the primary film forming agent has a relatively high acid value, such as for example an acid value (number) ranging from about 40 to about 95, preferably from about 50 to about 90, and preferably from about 60 to about 80, including all ranges and subranges therebetween.

Commercially available examples of the primary film forming polymers include but are not limited to, for example, those sold under the Isocryl® name by Estron Chemicals such as, for example, Isocryl C-70 (styrene/acrylates copolymer), Isocryl N-2513, Isocryl H-60, and Isocryl H-1871.

Preferably, the primary film former(s) are present in the compositions of the present invention in amounts ranging from about 0.5% to about 20% by weight, preferably from about 1% to about 15%, and preferably from about 2% to about 10%, by weight, based on the total weight of the composition, including all ranges and subranges in between.

Secondary Film Former

According to preferred embodiments, the compositions of the present invention may also optionally include at least one secondary film forming agent chosen from epoxy resins. Suitable examples of epoxy resins include those disclosed in U.S. Pat. No. 5,001,175, the entire contents of which is hereby incorporated by reference.

Preferably, suitable epoxy resins have a glass transition temperature (Tg) of less than about 100° C., preferably less than about 80° C. Non-limiting examples of suitable epoxy resins include tosylamide epoxy resins, such as those sold by Estron Chemical under the tradename Polytexm, e.g., E-75, E-100, and NX-55, NX-3214). Other non-limiting examples of suitable epoxy resins include aryl-sulfonamide epoxy resins.

According to preferred embodiments, if present, the at least one secondary film former is present in the invention compositions in an amount ranging from about 0.1% to about 50% by weight, preferably from about 1% to about 40% by weight, and preferably from about 3% to about 15% by weight, including all ranges and subranges therebetween, all weights being based on the total weight of the composition.

Co-Film Formers

According to preferred embodiments, the compositions of the present invention may also optionally include at least one co-film forming agent. Suitable co-film forming agents include, but are not limited to, (meth)acrylate homopolymers and copolymers, polyurethanes, polyacryls, polymethacryls, cellulosic polymers, styrene-acryl copolymers, polystyrene-polyacryl mixtures, polysiloxanes, polyethers, polyesters, urethane-acryl copolymers, cellulose acetate propionate, siloxane-urethane copolymers, polyurethane-polymethacryl mixtures, silicone-acryl copolymers, vinyl acetate polymers, and mixtures thereof.

Suitable co-film forming agents also include aldehyde condensation products such as arylsulfonamide formaldehyde resins, specifically toluene sulfonamide formaldehyde resin which is a condensation product of formaldehyde and toluene sulfonamide, toluene sulfonamide/epoxy resins, e.g. tosylamide and non-drying alkyd resins, acrylic polymers and copolymers, polyurethane, polyacryls, polymethacryls, styrene-acryl copolymers, polystyrene-polyacryl mixtures, polysiloxanes, polyethers, polyesters, urethane-acryl copolymers, siloxane-urethane copolymers, polyurethane-polymethacryl mixtures, vinyl acetate polymers, and mixtures thereof.

Suitable co-film forming agents also include polyester resins formed by reacting a polyhydric alcohol with a polybasic acid, e.g., phthalic acid, such as the commercial product sold by Unitex Chemical Corporation under the name UNIPLEX 670-P, which is a polyester resin obtained by reacting trimellitic acid, neopentyl glycol, and adipic acid. (Meth)acrylic resins according to the disclosure may include copolymers of methyl methacrylate with butyl acrylate, butyl methacrylate, isobutyl methacrylate, or isobornyl methacrylate, for example, the commercial products PARALOID DM-55, PARALOID B48N, PARALOID B66, and ELVACITE 2550; copolymers of isobutylmethacrylate and butyl methacrylate, for instance, the commercial product ELVACITE 2046; and isobutyl methacrylate polymers, for example, PARALOID B67.

Suitable co-film forming agents also include polymers of natural origin, such as plant resins such as dammars, elemi, copals, benzoin; gums such as shellac, sandarac and mastic.

Specific examples of suitable co-film forming agents include, but are not limited to phthalic anhydride/glycerin/glycidyl decanoate copolymer, adipic acid/neopenttyl glycol/trimellitic anhydride copolymer, tosylamide/epoxy resin, butyl acetate (and) acrylates copolymer, and hydrogenated acetophenone/oxymethylene copolymer.

Preferably, if present, the at least one co-film forming agents are added to the nail compositions of the present invention in an amount ranging from about 0.1 to 10 percent, preferably from about 0.2 to 8 percent, preferably from about 0.5 to about 5 percent by weight of the total weight of the composition, including all ranges and subranges there between.

Silicone Acrylate Copolymer

According to preferred embodiments, the compositions of the present invention may also optionally include at least one silicone acrylate copolymer.

Preferably, suitable silicone acrylate copolymers have a glass transition temperature (Tg) of greater than 20° C., preferably greater than about 25° C.

Suitable examples of silicone acrylate copolymers include silicone/(meth)acrylate copolymers, such as those described in U.S. Pat. Nos. 5,061,481, 5,219,560, 5,262,087 and US 2012/0301415, the entire contents of all of which are hereby incorporated by reference.

Suitable examples also include polymers derived from non-polar silicone copolymers comprising repeating units of at least one polar (meth)acrylate unit and vinyl copolymers grafted with at least one non-polar silicone chain. Non-limiting examples of such copolymers are acrylates/dimethicone copolymers such as those commercially available from Shin-Etsu, for example, the products sold under the tradenames KP-545 (cyclopentasiloxane (and) acrylates/dimethicone copolymer), KP-543 (butyl acetate (and) acrylates/dimethicone copolymer), KP-549 (methyl trimethicone (and) acrylates/dimethicone copolymer), KP-550 (tentative INCI name: isododecane (and) acrylate/dimethicone copolymer), and mixtures thereof. Additional examples include the acrylate/dimethicone copolymers sold by Dow Corning under the tradenames FA 4001 CM SILICONE ACRYLATE (cyclopentasiloxane (and) acrylates/polytrimethylsiloxymethacrylate copolymer) and FA 4002 ID SILICONE ACRYLATE (isododecane (and) acrylates/polytrimethylsiloxymethacrylate Copolymer), and mixtures thereof.

Suitable examples also include polymers comprising a backbone chosen from vinyl polymers, methacrylic polymers, and acrylic polymers, and at least one chain chosen from pendant siloxane groups. Non-limiting examples of such polymers and their synthesis are disclosed, for example, in U.S. Pat. Nos. 4,972,037, 5,061,481, 5,209,924, 5,849,275, and 6,033,650, and WO 93/23446, WO 95/06078 and WO 01/32737, the disclosures of all of which are hereby incorporated by reference. These polymers may be sourced from various companies. One such company is Minnesota Mining and Manufacturing Company which offers these types of polymers under the tradenames "Silicone Plus" polymers (for example, poly(isobutyl methacrylate-co-methyl FOSEA)-g-poly(dimethylsiloxane), sold under the tradename SA 70-5 IBMMF).

Suitable examples also include silicone/acrylate graft terpolymers, for example, the copolymers described in WO 01/32727 A1, the disclosure of which is hereby incorporated by reference.

Suitable examples also include polymers comprises a backbone chosen from vinyl backbones, methacrylic backbones, and acrylic polymeric backbones and further comprises at least one pendant siloxane group. Non-limiting examples of such polymers are disclosed in U.S. Pat. Nos. 4,693,935, 4,981,903, and 4,981,902, the disclosures of which are hereby incorporated by reference.

Suitable examples also include those described in U.S. Pat. No. 5,468,477, the disclosure of which is hereby incorporated by reference. A non-limiting example of these polymers is poly(dimethylsiloxane)-g-poly(isobutyl methacrylate), which is commercially available from 3M Company under the tradename VS 70 IBM.

Preferably, if present, the at least one silicone acrylate copolymer is present in the compositions of the present invention in an amount ranging from about 0.1 percent to about percent by weight, preferably from about 0.5 percent to about 8.5 percent, and preferably from about 0.25 percent to about 5 percent by weight, including all ranges and subranges therebetween, all weights being based on the total weight of the composition.

Thixotropic Agent

According to preferred embodiments, the compositions of the present invention may also optionally include at least one thixotropic agent in an amount that is sufficient to give the composition a viscosity at rest sufficient to give it the desired texture and thixotropic behavior.

In at least one embodiment, the nature and/or amount of the at least one thixotropic agent is such that, in response to a non-chemical action, for instance, a mechanical action, prior to or simultaneously with the application of the composition to the nails, the viscosity of the composition may be reversibly lowered to a value less than or equal to 0.4 Pa·s, for example, less than or equal to 0.3 Pa·s.

The at least one thixotropic agent may be chosen, for example, from hydrophilic or organophilic clays, hydrophilic or hydrophobic fumed silicas, elastomeric organopolysiloxanes, and mixtures thereof.

Clays are silicates containing a cation that may be chosen from calcium, magnesium, aluminium, sodium, potassium, and lithium cations, and mixtures thereof. As used herein, the term "hydrophilic clay" means a clay that is capable of swelling in water; this clay swells in water and forms after hydration a colloidal dispersion.

Examples of such products include, but are not limited to, clays of the smectite family such as montmorillonites, hectorites, bentonites, beidellites, and saponites, clays of the vermiculite family, stevensite, and chlorites.

These clays may be of natural or synthetic origin.

Non-limiting examples of hydrophilic clays include smectites such as saponites, hectorites, montmorillonites, bentonites, beidellite and, in at least one embodiment, synthetic hectorites (also known as laponites), for instance, the products sold by the company Laporte under the names Laponite XLG, Laponite RD, and Laponite RDS (these products include, for example, sodium magnesium silicates and sodium lithium magnesium silicates); bentonites, for instance the product sold under the name Bentone HC by the company Rheox; magnesium aluminium silicates, which may be hydrated, for instance, the products sold by the company Vanderbilt Company under the names Veegum Ultra, Veegum HS, and Veegum DGT, and calcium silicates, such as the product in synthetic form sold by the company under the name Micro-cel C.

The organophilic clays are clays modified with chemical compounds that make the clay capable of swelling in solvent media.

The clay may be chosen, for example, from montmorillonite, bentonite, hectorite, attapulgite, sepiolite, and mixtures thereof. In one embodiment, the clay is chosen from bentonite and hectorite.

The chemical compound used to modify the organophilic clay may be chosen, for instance, from quaternary amines, tertiary amines, amine acetates, imidazolines, amine soaps, fatty sulfates, alkyl aryl sulfonates, amine oxides, and mixtures thereof.

Suitable organophilic clays include, but are not limited to, quaternium-18 bentonites such as those sold under the names Bentone 3, Bentone 38, Bentone 27 V CG, and Bentone 38V by the company Elementis, Tixogel VP by the company United Catalyst, and Claytone 34, Claytone 40, and Claytone XL by the company Southern Clay; stearalkonium bentonites such as those sold under the names Bentone 27V by the company Elementis, Tixogel LG by the company United Catalyst, and Claytone AF and Claytone APA by the company Southern Clay; and quaternium-18/benzalkonium bentonites such as those sold under the names Claytone HT and Claytone PS by the company Southern Clay.

The hydrophilic fumed silicas may be obtained by high-temperature hydrolysis of a volatile silicon compound in an oxyhydric flame, producing a finely divided silica. Hydrophilic silicas have a large number of silanol groups at their surface. Such hydrophilic silicas are sold, for example, under the names Aerosil 130(R), Aerosil 200(R), Aerosil 255(R), Aerosil 300(R), and Aerosil 380(R) by the company Degussa, and Cab-O-Sil HS-5(R), Cab-O-Sil EH-5(R), Cab-O-Sil LM-130(R), Cab-O-Sil MS-55(R), and Cab-O-Sil M-5(R) by the company Cabot.

The hydrophobic fumed silicas may be obtained by modification of the surface of the silica via a chemical reaction that generates a reduction in the number of silanol groups, these groups possibly being substituted, for example, with hydrophobic groups.

The hydrophobic groups may be chosen, for instance, from:

trimethylsiloxyl groups, which may be obtained by treating fumed silica in the presence of hexamethyldisilazane. Silicas thus treated are known as "Silica silylate" according to the CTFA (6th edition, 1995). They are sold, for example, under the references Aerosil R812(R) by the company Degussa, and Cab-O-Sil TS-530(R) by the company Cabot, dimethylsilyloxyl or polydimethylsiloxane groups, which may be obtained by treating fumed silica in the presence of polydimethylsiloxane or dimethyldichlorosilane. Silicas thus treated are known as "Silica dimethyl silylate" according to the CTFA (6th edition, 1995). They are sold, for example, under the references Aerosil R972(R) and Aerosil R974(R) by the company Degussa, and Cab-O-Sil TS-610 (R) and Cab-O-Sil TS-720(R) by the company Cabot.

According to one embodiment, the at least one thixotropic agent is chosen from organophilic modified clays such as hectorite modified with benzyldimethylammonium stearate.

The thixotropic agent, if present, may be present in the composition in an amount greater than or equal to 0.05 percent by weight, for example, ranging from 0.05 percent to 15 percent by weight, or greater than or equal to 0.5 percent by weight, for example, ranging from 0.5 percent to 10 percent by weight, or ranging from 0.9 percent to 7.5 percent by weight, relative to the total weight of the composition, including all ranges and subranges therebetween.

Fillers

According to preferred embodiments, the compositions of the present invention may also optionally include at least one filler. Suitable examples of fillers include mineral or organic particles of any shape, in sheet, spherical or oblong form, regardless of the crystallographic shape (for example sheet, cubic, hexagonal, orthorhombic, etc). Mention may be made of talc, mica, kaolin, polyamide (Nylon®) (Orgasol® from Atochem), poly-3-alanine and polyethylene powders, tetrafluoroethylene polymer powders (Teflon®), lauroyl-lysine, starch, boron nitride, acrylic acid copolymers (Polytrap® from Dow Corning) and silicone resin microbeads (Tospearls® from Toshiba, for example), elastomer polyorganosiloxane particles, precipitated calcium carbonate, magnesium carbonate and hydro-carbonate, hydroxyapatite, glass or ceramic microcapsules, metallic soaps derived from carboxylic organic acids having 8 to 22 carbon atoms, preferably from 12 to 18 carbon atoms, for example zinc, magnesium or lithium stearate, zinc laurate, magnesium myristate.

Fillers, if present, can be present particularly at a content ranging from about 0.01% to about 10% by weight, preferably ranging from about 0.1% to about 5% by weight, most preferably from about 0.5% to about 1.5%, in relation to the total weight of the inventive compositions, including all ranges and subranges therebetween.

Coloring Agent

According to preferred embodiments, the compositions of the present invention may also optionally include at least one coloring agent. Preferably, the at least one coloring agent is chosen from the group consisting of soluble dyes, pigments, nacres and glitter.

The term "soluble dyes" should be understood to refer to organic, inorganic or organometallic compounds, soluble in the composition according to the invention and intended to color said composition.

Suitable dyes are, for example, Sudan Red, DC Red 17, DC Green 6, -carotene, soybean oil, Sudan brown, DC Yellow 11, DC Violet 2, DC Orange 5 and Quinoline Yellow.

The term "nacres" should be understood to refer to iridescent particles of any shape, particularly produced by some mollusks in their shell or by synthetic means.

The term "pigments" should be understood to refer to inorganic or organic, white or colored particles of any shape, insoluble in the composition according to the invention and intended to color said composition.

The pigments may be white or colored, inorganic and/or organic. Of the inorganic pigments, mention may be made of titanium dioxide, optionally surface-treated, zirconium or cerium oxides, along with zinc, iron (black, yellow or red) or chromium oxides, manganese violet, ultramarine blue, chromium hydrate and iron blue, metallic powders such as aluminum powder, copper powder.

Of the organic pigments, mention may be made of carbon black, D & C type pigments, and lacquers based on cochineal carmine, barium, strontium, calcium, aluminum.

Mention may also be made of effect pigments such as particles comprising a natural or synthetic organic or inorganic substrate, for example glass, acrylic resins, polyester, polyurethane, polyethylene terephthalate, ceramics, aluminas and optionally coated with metallic substances such as aluminum, gold, copper, bronze, or with metal oxides such as titanium dioxide, iron oxide, chromium oxide, inorganic or organic pigments and mixtures thereof.

The pearlescent pigments may be chosen from white pearlescent pigments such as mica coated with titanium, or bismuth oxychloride, colored pearlescent pigments such as titanium mica coated with iron oxides, titanium mica coated with iron blue and chromium oxide in particular, titanium mica coated with an organic pigments of the aforementioned type and pearlescent pigments based on bismuth oxychloride.

Pigments with goniochromatic properties may be used, particularly liquid crystal or multilayer pigments. Optical brighteners or fibers optionally coated with optical brighteners may also be used.

The at least one coloring agent, if present, is preferably present in a total content greater than or equal to 0.1% by weight in relation to the total weight of the layer, ranging preferably from about 0.1 to about 5%, advantageously from about 0.2 to about 3% by weight in relation to the total weight of the composition, including all ranges and subranges therebetween.

Solvents

According to preferred embodiments, the compositions of the present invention may also optionally include at least one solvent chosen from organic and inorganic solvents. Suitable solvents may particularly be chosen from:

liquid ketones at ambient temperature such as methylethylketone, methylisobutylketone, diisobutylketone, isophorone, cyclohexanone and acetone, liquid alcohols at ambient temperature such as ethanol, isopropanol, diacetone-alcohol, 2-butoxyethanol and cyclohexanol, liquid glycols at ambient temperature such as ethyleneglycol, propyleneglycol, pentyleneglycol and glycerol, liquid propyleneglycol ethers at ambient temperature such as propyleneglycol monomethylether, propyleneglycol monomethyl ether acetate and dipropyleneglycol mono-n-butylether, short-chain esters (comprising in total from 3 to 8 carbon atoms) such as ethyl acetate, methyl acetate, propyl acetate, n-propyl acetate, iso-propyl acetate, n-butyl acetate, iso-butyl acetate, ter-butyl acetate and isopentyl acetate, liquid alkanes at ambient temperature such as decane, heptane, dodecane and cyclohexane, liquid aromatic hydrocarbons at ambient temperature such as toluene and xylene, liquid silicones at ambient temperature, and mixtures thereof.

The compositions according to the invention may also comprise so-called volatile solvents.

The term "volatile solvent" refers to a solvent capable of evaporating on contact with keratin matter, in less than one hour, at ambient temperature and at atmospheric pressure.

The volatile solvents according to the invention are preferably liquid solvents at ambient temperature, having a vapor pressure different to zero, at ambient temperature and atmospheric pressure, particularly ranging from 0.13 Pa to 40,000 Pa (from $10^{-3}$ to 300 mm Hg), particularly ranging from 1.3 Pa to 13,000 Pa (from 0.01 to 100 mm Hg), and more specifically ranging from 1.3 Pa to 1300 Pa (from 0.01 to 10 mm Hg).

On the other hand, a "non-volatile solvent" evaporates on contact with keratin matter in more than one hour, at ambient temperature and atmospheric pressure.

Preferably, the compositions of the present invention comprise a solvent chosen from acetone, ethyl acetate, propyl acetate, butyl acetate, isopropyl alcohol, and mixtures thereof.

Preferably, the total solvent content in the inventive nail compositions is above about 15%, preferably above about 20%, and preferably above about 30% by weight in relation to the total weight of the composition.

Auxiliaries/Additives

According to preferred embodiments, the compositions of the present invention may also optionally include at least one additive or auxiliary commonly used in cosmetic compositions and known to a person skilled in the art as being capable of being incorporated into said compositions. Such additives or auxiliaries may be chosen from preservatives, fragrances, oils, waxes, surfactants, antioxidants, agents for combating free radicals, spreading agents, wetting agents, dispersing agents, antifoaming agents, neutralizing agents, stabilizing agents, active principles chosen from essential oils, UV screening agents, sunscreens, moisturizing agents, vitamins, actives, proteins, ceramides, plant extracts, fibers, and the like, wetting agents and their mixtures.

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture. These additives may be present in the color coat or top coat composition in a proportion from about 0% to about 10%, such as from about 0.01% to about 7% relative to the total weight of the composition and further such as from about 0.1% to about 5%, including all ranges and subranges therebetween.

Needless to say, the composition of the invention should be cosmetically or dermatologically acceptable, i.e., it should contain a non-toxic physiologically acceptable. The composition may be in any galenic form normally employed in the cosmetic and dermatological fields which is suitable for topical administration onto nails.

According to preferred embodiments of the present invention, methods for making up and/or protecting nails comprising applying to the nails at least one nail composition of the present invention in an amount sufficient to makeup or protect the nails using an applicator of the present invention are provided.

The following Examples are intended to be non-restrictive and explanatory only, with the scope of the invention being defined by the claims.

Example 1

Method of Preparation of Inventive Compositions

Color coat: All ingredients with the exception of colorants, dimethicone and silicone acrylate were combined together and mixed with a high-speed cutting blade for 30 minutes. Then the remaining ingredients were added. The final composition was mixed by 1400 classic shaker from Red Devil Equipment Corporation for 30 minutes or with a cutting-blade. The composition was left for at least 24 hours at room temperature (18-25° C.)

Top Coat: All ingredients were combined together and mixed for minutes by 1400 classic shaker from Red Devil Equipment Corporation for 30 minutes or with a cutting-blade.

Example 2

Exemplary Invention Color Coat Compositions

Inventive color coat compositions are set forth below.

| Function | INCI name | Inventive color coat 1 (% wt) * | Inventive color coat 2 (% wt) * |
|---|---|---|---|
| wetting agent | DIMETHICONE | 0.1 | 0.1 |
| sun filter | BENZOPHENONE-1 | 0.04 | 0.04 |
| solvent | ISOPROPYL ALCOHOL | 0.35 | 0.35 |
| solvent | ETHYL ACETATE | 19.69 | 19.59 |
|  | ETHYL ACETATE | 16.91 | 16.82 |
| adhesive agent | NITROCELLULOSE ISOPROPYL ALCOHOL | 8.89 3.81 | 8.84 3.79 |
| thickener | STEARALKONIUM HECTORITE | 0.99 | 0.98 |
| adhesive agent | NITROCELLULOSE ISOPROPYL ALCOHOL | 1.51 0.65 | 1.51 0.65 |
| pigment | BARIUM SULFATE RED 7 LAKE ROSIN | 0.24 0.18 0.03 | 0.24 0.18 0.03 |
| pigment | BARIUM SULFATE RED 6 LAKE ROSIN | 0.38 0.35 0.05 | 0.38 0.35 0.05 |
| pigment | TITANIUM DIOXIDE OXIDIZED POLYETHYLENE | 0.36 0.01 | 0.36 0.01 |
| sun filter | OCTOCRYLENE | 0.42 | 0.42 |
| plasticizer | ETHYL TOSYLAMIDE | 6.28 | 6.94 |
| solvent | PROPYL ACETATE | 0.75 | 0.75 |
| co-film former | ADIPIC ACID/NEOPENTYL GLYCOL/TRIMELLITIC ANHYDRIDE COPOLYMER | 0.3 | 0.3 |
| solvent | BUTYL ACETATE | 0.13 | 0.13 |
| co-film former | TOSYLAMIDE/EPOXY RESIN | 0.48 | 0.48 |
| solvent | BUTYL ACETATE | 0.16 | 0.16 |
| plasticizer | TRIBUTYL CITRATE | 0.63 | 0.63 |
| co-film former | BUTYL ACETATE ACRYLATES COPOLYMER | 0.12 0.12 | 0.12 0.12 |
| co-film former | HYDROGENATED ACETOPHENONE/ OXYMETHYLENE COPOLYMER | 0.24 | 0.24 |
| solvent | BUTYL ACETATE | 23.51 | 23.39 |
| active | CITRIC ACID | 0.04 | 0.04 |
| primary film former | STYRENE/ACRYLATES COPOLYMER[1] | 3.05 | 2.34 |
| secondary film former | TOSYLAMIDE EPOXY RESIN [2] BUTYL ACETATE | 6.46 2.27 | 6.42 2.26 |
| silicone acrylate copolymer | BUTYL ACETATE ACRYLATES/ DIMETHICONE COPOLYMER | 0.25 0.25 | 0.5 0.5 |

(% wt) * Overall weight of individual components present in the composition.
[1] Styrene/acrylates copolymer (Isocryl C-70) from Estron Chemical
[2] Tosylamide epoxy resin (Polytex NX-3214) from Estron Chemical

Example 3

Exemplary Invention Top Coat Compositions

Inventive top coat compositions are set forth below.

| Function | INCI name | Inventive top coat 1 (% wt) * | Inventive top coat 2 (% wt) * |
|---|---|---|---|
| colorant | VIOLET 2 | 0.00 | 0.00 |
| solvent | ETHYL ACETATE | 17.57 | 22.24 |
| solvent | ETHYL ACETATE | 17.27 | 12.61 |
| adhesive agent | NITROCELLULOSE ISOPROPYL ALCOHOL | 8.06 3.45 | 5.88 2.52 |
| adhesive agent | NITROCELLULOSE | 2.89 | 3.72 |
| solvent | ISOPROPYL ALCOHOL | 1.24 | 1.59 |
| adhesive agent | CELLULOSE ACETATE BUTYRATE | 3.36 | 3.50 |
| plasticizer | ETHYL TOSYLAMIDE | 6.74 | 8.00 |
| co-film former | PHTHALIC ANHYDRIDE/GLYCERIN/ GLYCIDYL DECANOATE COPOLYMER ETHYL ACETATE | 0.64 0.27 | 0.70 0.30 |
| solvent | BUTYL ACETATE | 36.70 | 36.94 |
| primary film former | STYRENE/ACRYLATES COPOLYMER[1] | 0.91 | 1.00 |
| silicone acrylate copolymer | ACRYLATES/DIMETHICONE COPOLYMER BUTYL ACETATE | 0.46 0.46 | 0.50 0.50 |

(% wt) * Overall weight of individual components present in the composition.
[1] Styrene/acrylates copolymer (Isocryl C-70) from Estron Chemical

Example 4

Comparative Compositions

As discussed below, inventive compositions were compared for various properties against the following comparator formulations:

Comparator A

Color coat: butyl acetate, ethyl acetate, nitrocellulose, acetyl tributyl citrate, isopropyl alcohol, adipic acid/neopentyl glycol/trimellitic anhydride copolymer, glycidoxypropyl polysilsesquioxane, stearalkonium bentonite, n-butyl alcohol, styrene/acrylates copolymer, titanium dioxide, barium sulfate, colophonium (rosin) (colophane), silica, benzophenone-1, pigment.

Top coat: ethyl acetate, butyl acetate, cellulose acetate butyrate, isopropyl alcohol, acetyl butyl citrate, glycidoxypropyl popysilsesquioxane, bis-hemapoly(1,4-butanediol)-22?IPDI copolymer, acrylates copolymer, adipic acid/neopentyl glycol/trimellitic anhydride copolymer, trimethylpentanediyl dibenzoate, acetone, bis-trimethylbenzoyl phenylphosphine oxide, benzophenone-3, pigment.

Comparator B

Color Coat: butyl acetate, ethyl acetate, nitrocellulose, acetyl tributyl citrate, isopropyl alcohol, tosylamide/epoxy resin, stearalkonium bentonite, triphenyl phosphate, glycidyl neodecanoate/phthalic anhydride/tmp crosspolymer, aqua/water/eau, adipic acid/neopentyl glycol/trimellitic anhydride copolymer, calcium aluminum borosilicate, calcium sodium borosilicate, synthetic fluorphlogopite, isosorbide dicaprylate/caprate, silica, diacetone alcohol, etocrylene, kaolin, hydroxyethyl acrylate/ipdi/ppg-15 glyceryl ether copolymer, acrylates/dimethicone copolymer, corallina officinalis extract, tocopheryl acetate, phosphoric acid, trimethylsiloxysilicate, dimethicone, cetyl peg/ppg-10/1 dimethicone, styrene/acrylates copolymer, polyvinyl butyral, carthamus tinctorius (safflower) seed oil, butylene glycol, macrocystis pyrifera (kelp) extract, hydrolyzed conchiolin protein, methylparaben, propylparaben, colorants.

Topcoat: ethyl acetate, butyl acetate, isopropyl alcohol, cellulose acetate butyrate, mek, adipic acid/neopentyl glycol/trimellitic anhydride copolymer, acetyl tributyl citrate, sucrose benzoate, n-butyl alcohol, ethyl trimethylbenzoyl phenylphosphinate, etocrylene, hydroxyethyl acrylate/ipdi/ppg-15 glyceryl ether copolymer, water, diamond powder, alumina, methyltriethoxysilane, platinum powder, silica, colorants Comparator C Color Coat: ethyl acetate, butyl acetate, propyl acetate, nitrocellulose, tosylamide epoxy resin, isopropyl alcohol, acetyl tributyl citrate, ethyl tosylamide, acrylates copolymer, stearalkonium hectorite, tributyl citrate, octocrylene, titanium dioxide, adipic acid/neopentyl glycol/trimellitic anhydride copolymer, hydrogenated acetophenone/oxymethylene copolymer, rosin, oxidized polyethylene, dimethicone, citric acid, benzophenone-1, colorants.

Topcoat: butyl acetate, ethyl acetate, nitrocellulose, ethyl tosylamide, isopropyl alcohol, cellulose acetate butyrate, acrylates copolymer, acetyl tributyl citrate, adipic acid/neopentyl glycol/trimellitic anhydride copolymer, violet 2.

Example 5

Evaluation of Inventive Compositions: Methods

Sample Preparation for In Vitro Testing:

In order to prepare samples of the inventive compositions and comparators compositions for in vitro tests, 6 mil of a tested product was applied on a substrate specific for a test by using a drawdown bar with a microprocessor controlled film applicator (Coatmaster 509 MC from Erichsen) at a speed of 25 mm/s. The samples were dried for 24 hours at room temperature.

In vitro shine (gloss) evaluation: A thin layer of a tested composition was applied on a drawdown chart (Byko-opacity chart 5C, 7.6×10.25 inch) according to the method described above. Gloss of the coating was measured at 20° by using the Micro-TRI-Gloss meter, available from BYK-Gardner and expressed by gloss units (GU).

In vitro hardness evaluation: A thin layer of a tested composition was applied on a glass plate (customer-made, 4×6 inch) by using the same method as described above. The hardness of the coatings was measured by Pendulum Hardness Tester (Persoz pendulum) equipped with a temperature and humidity control chamber (30±2° C., 70±2% RH) according to ASTM method D4366-95. In order to determine the hardness, number of oscillations of the pendulum during 1 minute was counted. Low number of oscillations (0-50 oscillations per minute) characterized soft material, while high number (>50 oscillations per minute) was typical for hard materials.

In vitro adhesion evaluation: A layer of the tested compositions were applied on Vitro-nails substrate from IMS test group according to the method described above. Adhesion properties were quantified by in-vitro method Reference ISO/DIN 2409, ASTM D3359. The adhesion properties were visually evaluated according to the scale below:

| Classification | Percent area removed |
| --- | --- |
| 5 | 0%-None |
| 4 | Less than 5% |
| 3 | 5-15% |
| 2 | 15-35% |
| 1 | 35-65% |
| 0 | Greater than 65% |

In vitro soapy water evaluation: The tested compositions were applied on plastic nail spoons from Daret Inc. Each nail spoon was treated with two coats of the tested composition, each coat was applied by a nail brush (the second coat was applied two minutes after the first coat) and then dried at room temperature for 24 hours. Then the spoons were immersed in a soapy water batch (1.4 g of Redken super-brew shampoo and 1 g of hand soap in 225 mL water) at 45° C. for 20 minutes and dried out with a cotton tissue. The dry samples were visually inspected for shine and color change, then abraded with a metal object (quarter) and again visually inspected for shine loss and/or color change on the surface. The scuffing was performed also for samples which were not exposed to the soapy water. All, samples were graded according to the following scale: "poor"—significant shine and color loss in comparison to the control sample (unscratched sample), "fair"—slight shine and color loss and "good"—almost no change in shine and color loss.

In vitro Young's modulus evaluation: A layer of tested product was applied according to the procedure already described on polypropylene (PP) substrate. The samples dried at room temperature (20-25° C.) for 4 to 7 days. Then, the film was removed from the substrate and cut by DMA film cutter from TA instrument (5.3 mm cutter, PN 984485.901 and Young's modulus was measured by using a Dynamic Mechanic Analyzer (Q800 from TA instruments) at 30° C. The hardness was expressed by Modulus values (MPa). Low number of MPa (0-100) characterized soft materials, while higher number (100-400) was typical for hard materials and very high number of MPa (>400) was specific for a very hard materials.

In vitro abrasion resistance: The abrasion resistance was tested on a BYK-Gardner™ 'Scrub' Abrasion Tester Model AG-8100. Each of the tested compositions was applied on a black Byko Charts scrub test panel by depositing the product as described above. The samples dried at room temperature (20-25° C.) for five days. Then the samples were scrubbed by a nylon brush (from BYK) with one kg load for 2×300 cycles with 30 cycles per minute. After the first 300 cycles, the brush was turned off. The gloss was measured before and after scrubbing using Micro-TRI-Gloss meter, available from BYK-Gardner, Columbia, Md. The reading at 60° degree was used for comparison. Following an arbitrary reading, it was determined that if the gloss damage was less than 10%, the abrasion resistance was defined as high, 10-20% as medium, and more than 20% as low.

Example 6

Evaluation of Inventive Compositions: Results

TABLE 3

Comparative studies of Inventive Compositions vs. Comparators A, B and C are set forth below: Comparison of color coat compositions*:

| | Shine at 20° | Persoz pendulum Hardness | Water resistance | Adhesion to Vitro Nails | Young's Modulus (MPa) |
| --- | --- | --- | --- | --- | --- |
| Comparator A | 50.3 | Low (49) | Fair | Good | Low (39) |
| Comparator B | 51.5 | High (75) | Fair | Good | High (148) |

TABLE 3-continued

Comparative studies of Inventive Compositions
vs. Comparators A, B and C are set forth below:
Comparison of color coat compositions*:

|  | Shine at 20° | Persoz pendulum Hardness | Water resistance | Adhesion to Vitro Nails | Young's Modulus (MPa) |
|---|---|---|---|---|---|
| Comparator C | 67 | Low (39) | Good | Good | Low (34) |
| Inventive 1 | 70.9 | Low (32) | Good | Good | Low (44) |
| Inventive 2 | 68.9 | Low (30) | Good | Good | Very Low (33) |

*Experiments for particular samples were conducted on the same day, however, the specific parameters were tested on different days. Shine and hardness were measured at different days under defined experimental conditions.

As per the results shown above, the inventive compositions had superior gloss comparing to tested comparators. The adhesion measurements of inventive 1 and 2 were at parity with the comparative compostions, while water resistance was better for inventive compositions than for comparator A and B and was at parity with comparator C. The measurements of hardness and Young's modulus for the inventive compostions were at parity with comparator A and C and lower than comparator B which indicates good wear of inventive compostions 1 and 2.

TABLE 4

Comparison of top coat compositions*:

|  | Shine at 20° | Persoza Pendulum Hardness | Water resistance | Young's Modulus (MPa) | Abrasion resistance |
|---|---|---|---|---|---|
| Comparator A | 69.1 | 185 | Good | 874 | Medium |
| Comparator B | 60.6 | 211 | Good | 1601 | Medium |
| Comparator C | 76.4 | 90 | Good | 438 | Medium |
| Inventive 3 | 80.2 | n/a | Good | 1161 | High |
| Inventive 4 | 81.4 | n/a | Good | 482 | High |

*Experiments for particular samples were conducted on the same day, however, the specific parameters were tested on different days. Shine and Young's modulus were measured at different days under defined experimental conditions. The presented data were collected on different days.

The preceding table lists the in vitro performance comparison of the inventive top coats compositions and comparators. As per the results, the inventive compositions had higher gloss values than the comparative compostions. The water resistance of the invetive compstions was at parity with the comparators and the abrasion resistance was higher. In addition, Young's modulus measurements were the highest for comparator B, followed by inventive compostion 3, comparator A, inventive compsotion 4 and comparator C. Those results show that the inventive compostion 3 was harder than inventive compsotion 4 and comparators A and C but less hard than comparator C. These parameters indicate good resistance to damage of inventive compostions.

Example 7

Plasticizers and Film Former Selection

In order to select the most suitable plasticizer for inventive compositions, various plasticizers were evaluated for shine according to the described method. The different plasticizers were incorporated into a base composition (Base) containing nitrocellulose (28%), isopropyl alcohol (12%) and butyl acetate (60%).

TABLE 5

Selection of plasticizers*

|  | Exp 1* | Exp 2* | Exp 3* | Exp 4* | Exp 5* | Exp 6* | Exp 7* | Exp 8* | Exp 9* |
|---|---|---|---|---|---|---|---|---|---|
| Base (42.86% in all exp.) | Yes | Yes | Yes | Yes | Yes | Yes | Yes | Yes | Yes |
| Ethyl tosylamide | 2% | 5% | 8% | — | — | — | — | — | — |
| sucrose acetate isobutyrate | — | — | — | 2.22% | 5.56% | 8.90% | — | — | — |
| acetyl tributyl citrate | — | — | — | — | — | — | 2% | 5% | 8% |
| Butyl acetate (QS in all exp) | 55.14% | 52.14% | 49.14% | 54.92% | 51.58% | 48.25% | 55.14% | 52.14% | 49.14% |
| Shine @ 20° | 73.9 | 77.7 | 81.4 | 67 | 65.5 | 70.1 | 69.1 | 69.9 | 70.4 |

*Experiments for presented examples were conducted on different days.

Based on the results provided above, ethyl tosylamide had the highest value of shine. It was followed by sucrose acetate isobutyrate and acetyl tributyl citrate.

TABLE 6

Selection of primary film formers*

| | Exp 1 | Exp 2 | Exp 3 | Exp 4 | Exp 5 | Exp 6 | Exp 7 |
|---|---|---|---|---|---|---|---|
| Base (as described above) | Yes | Yes | Yes | Yes | Yes | Yes | Yes |
| ethyl tosylamide | 5.00% | 5.00% | 5.00% | 5.00% | 5.00% | 5.00% | 5.00% |
| butyl acetate (and) acrylates copolymer | — | 6.67% | — | — | — | — | — |
| adipic acid/neopentyl glycol/trimellitic anhydride copolymer | — | — | 4.76% | — | — | — | — |
| tosylamide/epoxy resin | — | — | — | 4.44% | — | — | — |
| styrene/acrylates copolymer* | — | — | — | — | 6.67% | — | — |
| phthalic anhydride/glycerin/glycidyl decanoate copolymer | — | — | — | — | — | 4.76% | — |
| tosylamide epoxy resin (and) butyl acetate** | — | — | — | — | — | — | 4.44% |
| Butyl acetate (QS) | 52.14 | 45.47 | 47.38 | 47.70 | 45.47 | 47.38 | 47.70 |
| Shine @ 20° | 76.6 | 72.5 | 78.2 | 79.8 | 77.5 | 79.2 | 79.2 |
| Hardness | 281 | 294 | 238 | 243 | 278 | 274 | 250 |
| Adhesion | 2 | 0 | 0 | 1.75 | 2 | 1.75 | 3 |
| Young's Modulus (MPa) | 1732 | 987 | 121 | 984 | 1717 | 1724 | 940 |

*Experiments for each of the presented examples were conducted on different days.
**ISOCRYL C-70-STYRENE/ACRYLATES COPOLYMER
***POLYTEX NX-3214-TOSYLAMIDE EPOXY RESIN (74%) (and) BUTYL ACETATE (26%)

In order to evaluate primary film formers, six different compounds were incorporated into a base composition (Base) and were evaluated for shine, hardness, adhesion and Young's modulus. Based on the above presented measurements, compositions containing tosylamide/epoxy resin were characterized to have the highest value of shine, followed by phthalic anhydride/glycerin/glycidyl decanoate copolymer and tosylamide epoxy resin (and) butyl acetate, both generating the same shine.

As per results presented above, compositions containing styrene/acrylates copolymer, phthalic anhydride/glycerin/glycidyl decanoate copolymer and tosylamide epoxy resin (and) butyl acetate (epoxy resin) demonstrated better adhesion property than their counterparts. However, addition of adipic acid/neopentyl glycol/trimellitic anhydride copolymer enhanced the film with more flexibility than other film formers which illustrates that it can be a good plasticizer.

What is claimed is:

1. A nail care system comprising:
   a. at least one composition having a shine higher than about 60 GU at 20°, and
   b. at least one applicator comprising:
      a gripping portion,
      a stem extending from the gripping portion along a longitudinal axis X-X, wherein the stem comprises a succession of noncircular cross sections that are angularly offset with respect to one another about said axis X-X so as to form a helical pattern, wherein the succession of noncircular cross sections does not have a groove, and
      an applicator member fixed in a housing at the free end of the stem.

2. The nail care system of claim 1, wherein the stem has a succession of rectangular or oblong sections.

3. The nail care system of claim 2, where the composition comprises at least one adhesive agent; at least one primary film former; at least one plasticizer; and at least one solvent.

4. The nail care system of claim 1, wherein the stem has a succession of flattened sections.

5. The nail care system of claim 4, wherein at least one flattened section comprises a protuberance.

6. The nail care system of claim 4, where the composition comprises at least one adhesive agent; at least one primary film former; at least one plasticizer; and at least one solvent.

7. The nail care system of claim 6, where the weight ratio of the at least one primary film former to the at least one plasticizer in the composition is greater than or equal to about 1:1.

8. The nail care system of claim 6, wherein the at least one primary film former is a polymer having an acid value (number) ranging from about 40 to about 95.

9. The nail care system of claim 6, wherein the at least one primary film former has a Tg value ranging from about 40° C. to about 95° C.

10. The nail care system of claim 1, where the composition comprises at least one adhesive agent; at least one primary film former; at least one plasticizer; and at least one solvent.

11. The nail care system of claim 10, where the weight ratio of the at least one primary film former to the at least one plasticizer in the composition is greater than or equal to about 1:1.

12. The nail care system of claim 10, wherein the at least one primary film former is a polymer having an acid value (number) ranging from about 40 to about 95.

13. The nail care system of claim 10, wherein the at least one primary film former has a Tg value ranging from about 40° C. to about 95° C.

* * * * *